United States Patent
Sekiya et al.

(10) Patent No.: US 8,464,573 B2
(45) Date of Patent: Jun. 18, 2013

(54) GAS CONCENTRATION DETECTION SENSOR

(75) Inventors: Takayuki Sekiya, Nissin (JP); Kei Kosaka, Nagoya (JP); Sang Jae Lee, Ama-gun (JP)

(73) Assignee: NGK Insulators, Ltd., Nagoya (JP)

( * ) Notice: Subject to any disclaimer, the term of this patent is extended or adjusted under 35 U.S.C. 154(b) by 390 days.

(21) Appl. No.: 12/927,886

(22) Filed: Nov. 29, 2010

(65) Prior Publication Data

US 2011/0126610 A1 Jun. 2, 2011

(30) Foreign Application Priority Data

Nov. 27, 2009 (JP) ................. 2009-270400

(51) Int. Cl.
*G01N 7/00* (2006.01)
*G01N 27/26* (2006.01)

(52) U.S. Cl.
USPC ........................................ 73/23.31; 204/424

(58) Field of Classification Search
USPC ........ 73/23.31, 23.32, 23.33, 25.05; 123/672; 204/424, 428
See application file for complete search history.

(56) References Cited

U.S. PATENT DOCUMENTS

| 6,279,376 B1 | 8/2001 | Yamada et al. |
| 6,348,141 B1 * | 2/2002 | Kato et al. ..................... 204/428 |
| 7,390,385 B2 * | 6/2008 | Ikoma et al. .................. 204/428 |
| 2002/0195339 A1 | 12/2002 | Nakamura et al. |

FOREIGN PATENT DOCUMENTS

| EP | 1 046 906 | 10/2000 |
| JP | 10-177000 | 6/1998 |
| JP | 2005-195516 A1 | 7/2005 |

* cited by examiner

*Primary Examiner* — John Fitzgerald
*Assistant Examiner* — Nathaniel Kolb
(74) *Attorney, Agent, or Firm* — Burr & Brown

(57) ABSTRACT

A flow path from outer gas introduction apertures 144a to inner gas introduction apertures 134a has a narrower-width flow passage formed by an inner wall member 150. This structure effectively lowers the probability that a liquid, such as water, entering from the outer gas introduction apertures 144a passes through a gas inflow chamber 122 and reaches a sensor element 110, compared with a structure without the inner wall member 150. The inner wall member 150 is formed as a solid member that is capable of storing the surrounding heat. Even if there is a certain event that has the potential of causing a temperature decrease of the sensor element 110, for example, an abrupt change in flow rate of an object gas, the heat stored in the inner wall member 150 effectively prevents a temperature decrease of the sensor element 110. This structure prevents the occurrence of cracking in the sensor element 110, compared with a conventional sensor structure having a double-layered protective cover.

9 Claims, 12 Drawing Sheets

GAS CONCENTRATION DETECTION SENSOR

BACKGROUND OF THE INVENTION

1. Field of the Invention

The present invention relates to a gas concentration detection sensor.

2. Description of the Related Art

Gas concentration detection sensors have been known to detect the concentration of a selected gas, for example, NOx or oxygen, included in an object gas, such as emission or exhaust gas from an automobile. In the gas concentration detection sensors, the presence of water generated at an engine start time and adhering to a sensor element or an abrupt increase in flow rate of the object gas flowed against the sensor element may lower the temperature of the sensor element and cause cracking in the sensor element. One proposed measure for preventing the occurrence of cracking provides a protective cover to cover over the sensor element. For example, in a gas sensor disclosed in Patent Document 1, as one example of the protective cover, a protector of a double-layered structure with a vent for introducing the exhaust gas inside the gas sensor is provided around an outer circumference of an edge section of the sensor element.

Patent Document 1: JP 2005-195516 A (FIG. 10)

SUMMARY OF THE INVENTION

In the event of vibration or a relatively high flow rate of the object gas, the protective cover of this double-layered structure, however, cannot sufficiently prevent water from entering the protective cover via the vent and adhering to the sensor element to cool down the sensor element. This conventional structure also cannot sufficiently prevent a temperature decrease of the sensor element by the relatively high flow rate of the object gas. A protective cover has accordingly been demanded to more effectively prevent a temperature decrease of the sensor element and thereby the occurrence of cracking in the sensor element.

By taking into account the issue discussed above, an object of the present invention is to provide a gas concentration detection sensor having the structure of preventing the occurrence of cracking in a sensor element.

In order to attain at least part of the object above, a gas concentration detection sensor of the present invention is constructed as follows.

The gas concentration detection sensor of the invention includes: a sensor element that detects concentration of a selected gas included in an object gas; a first protection cover that covers over the sensor element and has a first gas introduction aperture allowing for a flow of the object gas from outside to inside of the first protection cover; a second protection cover that covers over the first protection cover and has a second gas introduction aperture allowing for a flow of the object gas from outside to inside of the second protection cover; and a gas flow path that runs from the second gas introduction aperture through a space between the first protection cover and the second protection cover to the first gas introduction aperture, enters inside of the first protection cover via the first gas introduction aperture, and reaches an edge of the sensor element. At least one of the first protection cover and the second protection cover is provided with an inner wall member of a solid form or a hollow form with an internal enclosed space arranged to at least partially narrow width of a flow path from the second gas introduction aperture to the first gas introduction aperture in the gas flow path.

In the gas concentration detection sensor according to one aspect of the invention, the inner wall member is arranged to at least partially narrow the width of the flow path from the second gas introduction aperture to the first gas introduction aperture in the gas flow path of the object gas. This structure effectively lowers the probability that a liquid, such as water, passes through the gas flow path and reaches the sensor element, compared with a structure without the inner wall member. The inner wall member in a solid form or a hollow form with an internal enclosed space is capable of storing the surrounding heat. Even if there is a certain event that has the potential of causing a temperature decrease of the sensor element, for example, an abrupt change in flow rate of the object gas, the heat stored in the inner wall member effectively prevents a temperature decrease of the sensor element. This structure prevents the occurrence of cracking in the sensor element, compared with a conventional sensor structure having a double-layered protective cover.

In one preferable embodiment of the gas concentration detection sensor of the invention, the first protection cover is provided with the inner wall member. In the gas concentration detection sensor of this embodiment, the inner wall member is located closer to the sensor element, compared with a structure having the inner wall member attached to only the second protection cover. This arrangement assures the enhanced effect of preventing a temperature decrease of the sensor element by the heat accumulated in the inner wall member.

In another preferable embodiment of the gas concentration detection sensor of the invention, the inner wall member has a specific heat equivalent to or higher than a specific heat of the first protection cover. The inner wall member can thus store a greater amount of the surrounding heat, compared with an inner wall member having a specific heat lower than the specific heat of the first protection cover.

In still another preferable embodiment of the gas concentration detection sensor of the invention, the gas flow path that causes the object gas to flow in from the second gas introduction aperture, pass through the space between the first protection cover and the second protection cover to the first gas introduction aperture by flowing in a direction from a free end to a base end of the sensor element, enter inside of the first protection cover via the first gas introduction aperture, flow in a direction from the base end to the free end of the sensor element, and reach the edge of the sensor element. There are a large number of bends in the gas flow path. Compared with a gas flow path having a less number of bends, the gas flow path having a greater number of bends effectively decreases the flow rate of the object gas in the gas flow path even in the event of an abrupt increase in flow rate of the object gas outside the second protection cover. The arrangement of this embodiment also lowers the probability that the liquid flowing in from the second gas introduction aperture passes through the gas flow path and reaches the sensor element, thus preventing a temperature decrease of the sensor element.

In another preferable embodiment of the gas concentration detection sensor of the invention, the inner wall member is formed separately from the first protection cover and the second protection cover. This separate structure facilitates fabrication of the gas concentration detection sensor, compared with an integrated structure where the inner wall member is integrally formed with the first protection cover or the second protection cover.

DETAILED DESCRIPTION OF THE INVENTION

Figure 1:
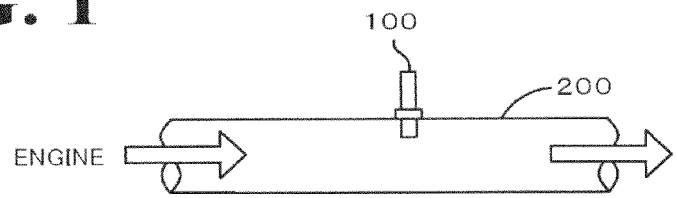
FIG. 1 is an explanatory diagrammatic view of a gas sensor 100 attached to piping 200.
Figure 2:
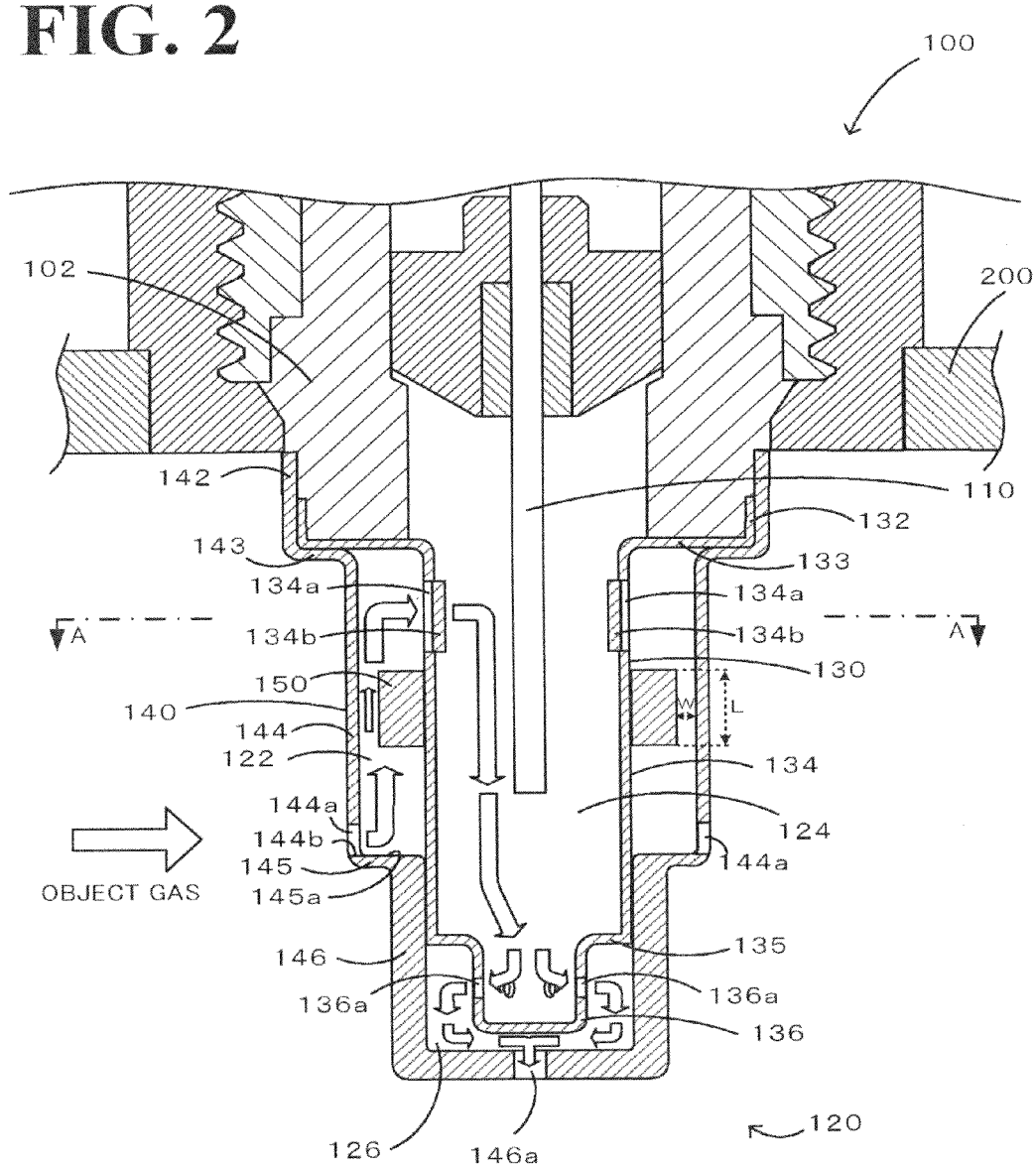
FIG. 2 is a vertical sectional view of the structure of the gas sensor 100.
Figure 3:
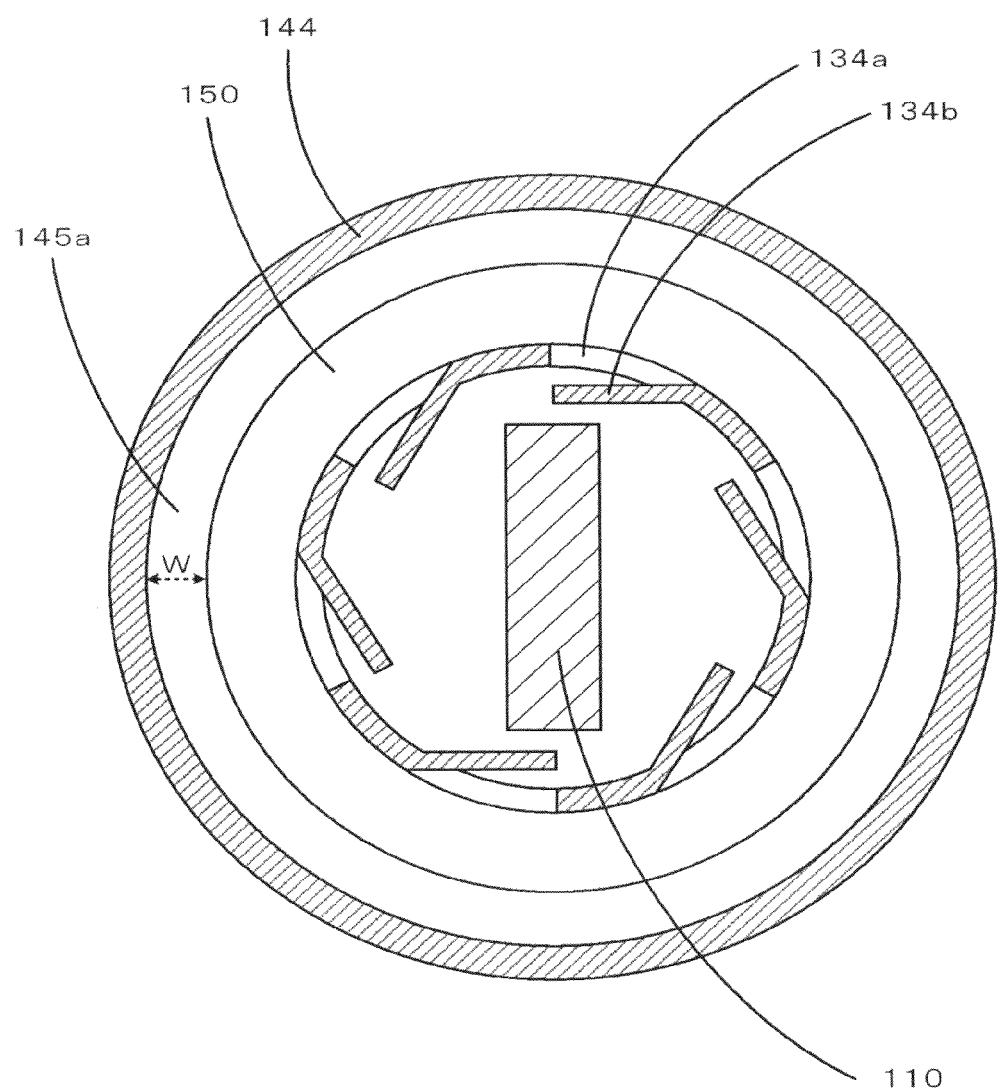
FIG. 3 is an A-A sectional view of FIG. 2.

One embodiment of practicing the present invention is described below with reference to the accompanied drawings. FIG. 1 is an explanatory view of a gas sensor 100 attached to piping 200. FIG. 2 is a vertical sectional view of the structure of the gas sensor 100. FIG. 3 is an A-A sectional view of FIG. 2.

As shown in FIG. 1, the gas sensor 100 is located inside the piping 200 formed as an exhaust path from a vehicle engine and is designed to detect the concentration of at least one gas component among various gas components, such as NOx and $O_2$, included in emission or exhaust gas from the engine as an object gas to be measured.

As shown in FIG. 2, the gas sensor 100 has a sensor element 110 having a function of measuring the concentration of a selected gas component included in the object gas to be measured, and a protective cover 120 protecting the sensor element 110.

The sensor element 110 is constructed as a long plate element having an oxygen ion conductive solid electrolyte layer of, for example, zirconia ($ZrO_2$). The sensor element 110 includes a built-in heater having a temperature control function of heating the sensor element 110 and keeping the sensor element 110 warm. This structure of the sensor element 110 and the principle of measuring the concentration of a gas component are known in the art and are described in, for example, Patent Document JP 2008-164411 A.

A protective cover 120 is arranged to surround the periphery of the sensor element 110. The protective cover 120 includes an inner protection cover 130 covering over an edge of the sensor element 110, an outer protection cover 140 covering over the inner protection cover 130, and an inner wall member 150 located between the inner protection cover 130 and the outer protection cover 140. A gas inflow chamber 122 and a gas outflow chamber 126 are formed as spaces defined by the inner protection cover 130 and the outer protection cover 140. A sensor element chamber 124 is formed as a space defined by the inner protection cover 130.

The inner protection cover 130 is a metal (for example, stainless steel) member having a cylindrical large-diameter section 132, a cylindrical stem section 134 having a smaller diameter than the diameter of the large-diameter section 132, and a bottomed cylindrical edge section 136 having a smaller diameter than the diameter of the stem section 134. The inner protection cover 130 also has a step element 133 connecting the large-diameter section 132 with the stem section 134 and a step element 135 connecting the stem section 134 with the edge section 136. The large-diameter section 132 has an inner circumference that is in contact with a metal main clamp 102, such that the inner protection cover 130 is fastened to the main clamp 102. The stem section 134 is located to cover over a side face of the sensor element 110. Six inner gas introduction apertures 134a formed to introduce the object gas from outside to inside of the inner protection cover 130 and six guide plates 134b provided to control the respective flows of the object gas running through the respective inner gas introduction apertures 134a are arranged respectively at equal intervals around the stem section 134 (see FIG. 3). The inner gas introduction apertures 134a and the guide plates 134b are arranged in one-to-one corresponding relation. Each of the guide plates 134b is located between corresponding one of the inner gas introduction apertures 134a and the sensor element 110. The multiple guide plates 134b are arranged to be rotationally symmetric (6-fold symmetry). Multiple (for example, six) inner gas discharge apertures 136a are formed to discharge the object gas from inside to outside of the inner protection cover 130 and are arranged at equal intervals around a side face of the edge section 136.

The outer protection cover 140 is a metal (for example, stainless steel) member having a cylindrical large-diameter section 142, a cylindrical stem section 144 having a smaller diameter than the diameter of the large-diameter section 142, and a bottomed cylindrical edge section 146 having a smaller diameter than the diameter of the stem section 144. The outer protection cover 140 also has a step element 143 connecting the large-diameter section 142 with the stem section 144 and a step element 145 connecting the stem section 144 with the edge section 146. The large-diameter section 142 has an inner circumference that is in contact with the metal main clamp 102 and with the large-diameter section 132, such that the outer protection cover 140 is fastened to the main clamp 102. The stem section 144 is located to cover over an outer circumferential face of the stem section 134. Multiple (for example, six) outer gas introduction apertures 144a are formed to introduce the object gas from outside to inside of the outer protection cover 140 and are arranged at equal intervals around the stem section 144. The outer gas introduction apertures 144a are circular holes formed in such a manner that a lower-most face 144b of an inner circumferential face of each outer gas introduction aperture 144a is aligned with an upper face 145a of the step element 145. The edge section 146 is formed as a thick member having a greater thickness than the thicknesses of the large-diameter section 142, the stem section 144, and the step element 145. An inner circumferential face of the edge section 146 is in contact with an outer circumferential face of the stem section 134. An outer gas discharge aperture 146a is formed in a bottom of the edge section 146 to discharge the object gas from inside to outside of the outer protection cover 140. The outer gas discharge aperture 146a is arranged on a central axis of the outer protection cover 140.

The inner wall member 150 is made of the same material as the inner protection cover 130 or alternatively a material having a higher specific heat than the specific heat of the material of the inner protection cover 130. The inner wall member 150 is a ring-shaped solid member having an inner diameter identical with an outer diameter of the stem section 134. The inner wall member 150 is attached to the outer circumferential face of the stem section 134 by, for example, welding. The inner wall member 150 is vertically located between a specific portion of the stem section 134 facing the outer gas introduction apertures 144a and the inner gas introduction apertures 134a.

The gas inflow chamber 122 is a space defined by the step element 133, the stem section 134, the stem section 144, and the step element 145. The object gas flows through the outer gas introduction apertures 144a into the gas inflow chamber 122, runs through the gas inflow chamber 122, and flows out through the inner gas introduction apertures 134a to the sensor element chamber 124. The inner wall member 150 is disposed in the gas inflow chamber 122, so that a gas flow path from the outer gas introduction apertures 144a to the inner gas introduction apertures 134a has a narrower-width flow passage defined by an inner circumferential face of the stem section 144 and an outer circumferential face of the inner wall member 150. The narrower-width flow passage may have dimensions that are not specifically restricted; for example, a width W (corresponding to a difference between a radius of the inner circumferential face of the stem section 144 and a radius of the outer circumferential face of the inner wall member 150) in a range of 0.1 to 1.5 mm and a length L in a gas flow direction (corresponding to a length in an axial direction of the inner wall member 150) in a range of 1 to 5 mm.

The sensor element chamber 124 is a space defined by the inner protection cover 130. The object gas flows through the inner gas introduction apertures 134a into the sensor element chamber 124, runs through the sensor element chamber 124, and flows out through the inner gas discharge apertures 136a to the gas outflow chamber 126. The gas outflow chamber 126 is defined by the step element 135, the edge section 136, and the edge section 146. The object gas flows through the inner gas discharge apertures 136a into the gas outflow chamber 126, runs through the gas outflow chamber 126, and is discharged from the outer gas discharge aperture 146a out of the protective cover 120.

The flow of the object gas in detection of the concentration of the gas component by the gas sensor 100 having the structure explained above is described below. The object gas running in the piping 200 flows via the outer gas introduction apertures 144a into the gas inflow chamber 122. The object gas flowing via the outer gas introduction apertures 144a passes through the gas inflow chamber 122 in a certain direction, which corresponds to a direction from a free end toward a base end of the sensor element 110, toward the inner gas introduction apertures 134a. The object gas then flows via the inner gas introduction apertures 134a, passes through the sensor element chamber 124 in an opposite direction toward the free end of the sensor element 110, and reaches the free end of the sensor element 110. At an engine start time, for example, when a liquid, such as water, is present inside the piping 200, the flow of the object gas may cause the liquid to be introduced via the outer gas introduction apertures 144a into the gas inflow chamber 122. The flow path from the outer gas introduction apertures 144a to the inner gas introduction apertures 134a in the gas inflow chamber 122 has the narrower-width flow passage formed by the inner wall member 150. The liquid has difficulty in passing through this narrower-width flow passage. Namely there is a low probability that the liquid flows via the narrower-width flow passage facing the inner wall member 150 and reaches a space closer to the inner gas introduction apertures 134a in the gas inflow chamber 122. When there is an abrupt increase in flow rate of the object gas running in the piping 200, resulting heat removal tends to abruptly decrease the temperature in any site that is in direct contact with the object gas. The solid inner wall member 150 provided in the periphery of the free end of the sensor element 110, however, stores the surrounding heat, so that the temperature on the free end of the sensor element 110 is kept by means of the inner wall member 150. The presence of the inner wall member 150 thus prevents an abrupt decrease of the temperature on the free end of the sensor element 110 even in the event of an abrupt increase in flow rate of the object gas. There are a large number of bends in the gas flow path from the outer gas introduction apertures 144a toward the free end of the sensor element 110. This structure effectively prevents the liquid from reaching the sensor element 110 and lowers the flow rate of the object gas in the gas flow path to prevent an abrupt increase of the flow rate in the neighborhood of the sensor element 110.

When the object gas reaches the free end of the sensor element 110, the sensor element 110 detects the concentration of the selected gas component included in the object gas. The object gas runs from the free end of the sensor element 110 toward the edge section 136 and flows radially outward from the center toward the outer circumference of the edge section 136 to go out through the inner gas discharge apertures 136a to the gas outflow chamber 126. The object gas then flows radially inward from the outer circumference toward the center of the edge section 146 in the gas outflow chamber 126 and is discharged outside via the outer gas discharge apertures 146a.

The respective components of this embodiment are correlated to the respective components of the invention. The sensor element 110 of the embodiment corresponds to the sensor element of the invention. The inner gas introduction apertures 134a, the inner protection cover 130, the outer gas introduction apertures 144a, and the outer protection cover 140 of the embodiment respectively correspond to the first gas introduction aperture, the first protection cover, the second gas introduction aperture, and the second protection cover of the invention. The gas inflow chamber 122 and the sensor element chamber 124 of the embodiment correspond to the gas flow path of the invention. The inner wall member 150 of the embodiment corresponds to the inner wall member of the invention.

In the structure of the embodiment described above, the flow path from the outer gas introduction apertures 144a to the inner gas introduction apertures 134a has the narrower-width flow passage formed by the inner wall member 150. This structure effectively lowers the probability that a liquid, such as water, passes through the gas inflow chamber 122 and reaches the sensor element 110, compared with a structure without the inner wall member 150. The inner wall member 150 is formed as a solid member that is capable of storing the surrounding heat. Even if there is a certain event that has the potential of causing a temperature decrease of the sensor element 110, the heat stored in the inner wall member 150 effectively prevents a temperature decrease of the sensor element 110. This structure of the embodiment prevents the occurrence of cracking in the sensor element 110, compared with a conventional sensor structure having a double-layered protective cover.

Figure 4:
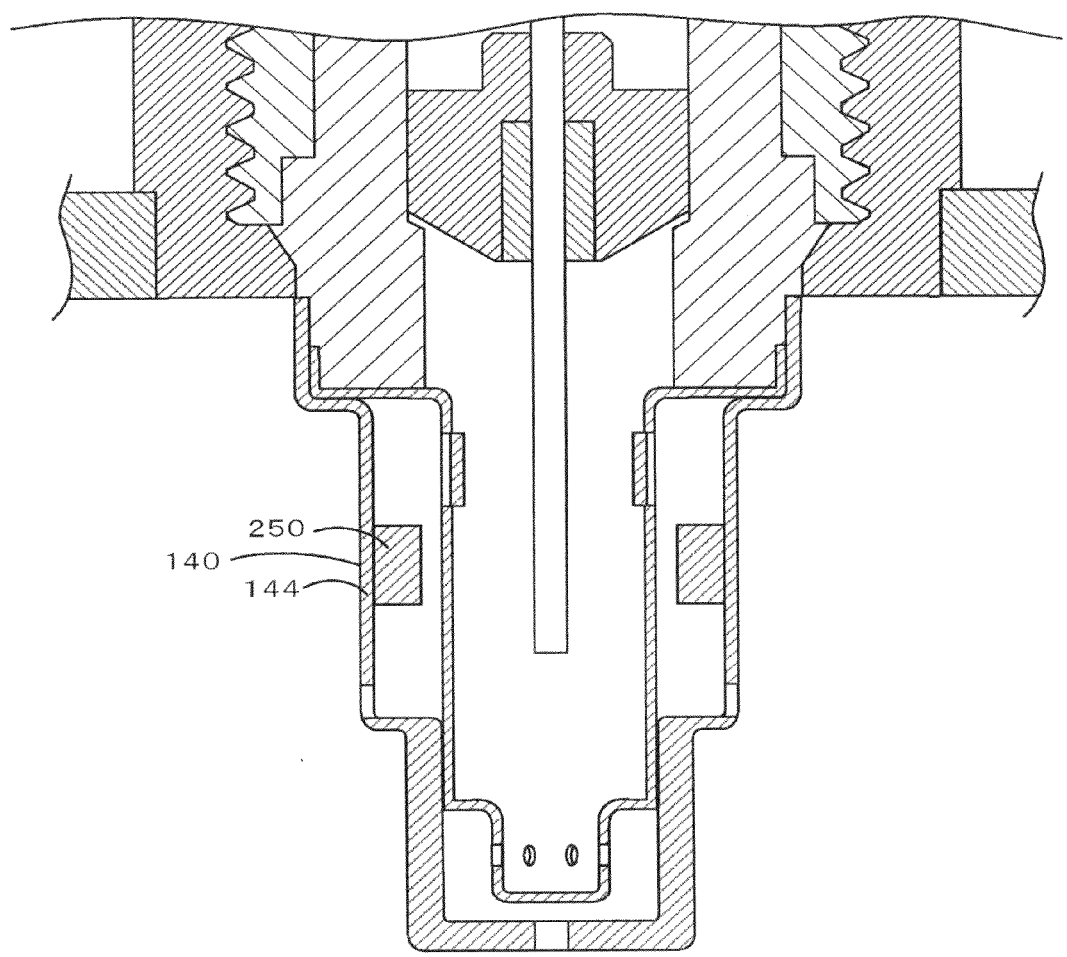
FIG. 4 is a vertical sectional view of an inner wall member 250 in one modified structure.

In the structure of the embodiment, the inner wall member 150 is attached to the outer circumferential face of the stem section 134 of the inner protection cover 130. The inner wall member 150 is located closer to the sensor element 110, compared with a structure of FIG. 4 where an inner wall member 250 is attached to the inner circumferential face of the stem section 144 of the outer protection cover 140. This structure of the embodiment effectively utilizes the heat stored in the inner wall member 150 to prevent a temperature decrease of the sensor element 110.

The inner wall member 150 has the specific heat substantially equivalent to or higher than the specific heat of the inner protection cover 130. The inner wall member 150 can thus store a greater amount of the surrounding heat, compared with an inner wall member having a specific heat lower than the specific heat of the inner protection cover 130.

In the gas flow path from the outer gas introduction apertures 144a toward the free end of the sensor element 110, the object gas flows via the outer gas introduction apertures 144a through the gas inflow chamber 122 in the direction corresponding to the direction from the free end toward the base end of the sensor element 110, toward the inner gas introduction apertures 134a, runs via the inner gas introduction apertures 134a through the sensor element chamber 124 in the direction toward the free end of the sensor element 110, and reaches the free end of the sensor element 110. Compared with a flow path having a less number of bends, the flow path with a large number of bends from the outer gas introduction apertures 144a toward the free end of the sensor element 110 effectively prevents the liquid from reaching the sensor element 110 and lowers the flow rate of the object gas therein. This arrangement prevents a temperature decrease of the sensor element 110 and thereby the occurrence of cracking.

The inner wall member 150 is formed as a separate component from the inner protection cover 130 and is readily attachable to the inner protection cover 130 by, for example, welding.

In the gas sensor 100 of the embodiment, the lower-most face 144b of the inner circumferential face of each outer gas introduction aperture 144a is aligned with the upper face 145a of the step element 145. Even when the liquid, such as water, present in the piping 200 at the engine start time enters the gas inflow chamber 122 via the outer gas introduction apertures 144a, there is no obstruction of interfering with the outflow of the liquid via the outer gas introduction apertures 144a out of the outer protection cover 140. Namely this arrangement facilitates the discharge of the liquid entering the gas inflow chamber 122 and thereby effectively prevents the occurrence of cracking due to a liquid-inducing temperature decrease of the sensor element 110.

The guide plates 134b control the flows of the object gas via the inner gas introduction apertures 134a into the sensor element chamber 124 to prevent direct approach of the object gas flows toward the sensor element 110. Compared with a structure without the guide plates 134b, this structure of the embodiment effectively prevents a temperature decrease of the sensor element 110 caused by the flows of the object gas and thereby the occurrence of cracking.

In the gas flow path from the sensor element chamber 124 to the outer gas discharge aperture 146a, the object gas flows radially outward from the center toward the outer circumference of the inner protection cover 130 to go out through the inner gas discharge apertures 136a to the gas outflow chamber 126, flows radially inward from the outer circumference toward the center of the outer protection cover 140 in the gas outflow chamber 126, and is discharged outside via the outer gas discharge apertures 146a. This structure has a greater number of bends formed in the flow path, compared with a structure with the inner gas discharge apertures 136a formed in a bottom face of the edge section 136. This structure of the embodiment prevents the liquid, such as water, entering the gas outflow chamber 126 via the outer gas discharge apertures 146a from reaching the sensor element 110, thus preventing the occurrence of cracking in the sensor element 110.

The edge section 146 has the greater thickness than those of the large-diameter section 142, the stem section 144, and the step element 145. The greater thickness of the edge section 146 leads to the greater length of the outer gas discharge aperture 146a and prevents the liquid from entering the gas outflow chamber 126 via the outer gas discharge aperture 146a. The outer gas discharge aperture 146a is open in a direction perpendicular to the flow of the object gas in the piping 200. This arrangement also prevents the liquid from entering the gas outflow chamber 126 via the outer gas discharge aperture 146a. Such structures function to prevent the liquid from entering via the outer gas discharge aperture 146a and reaching the sensor element 110.

The invention is not limited to the embodiment discussed above but may be actualized in diversity of other embodiments and applications within the scope of the invention.

Figure 5:
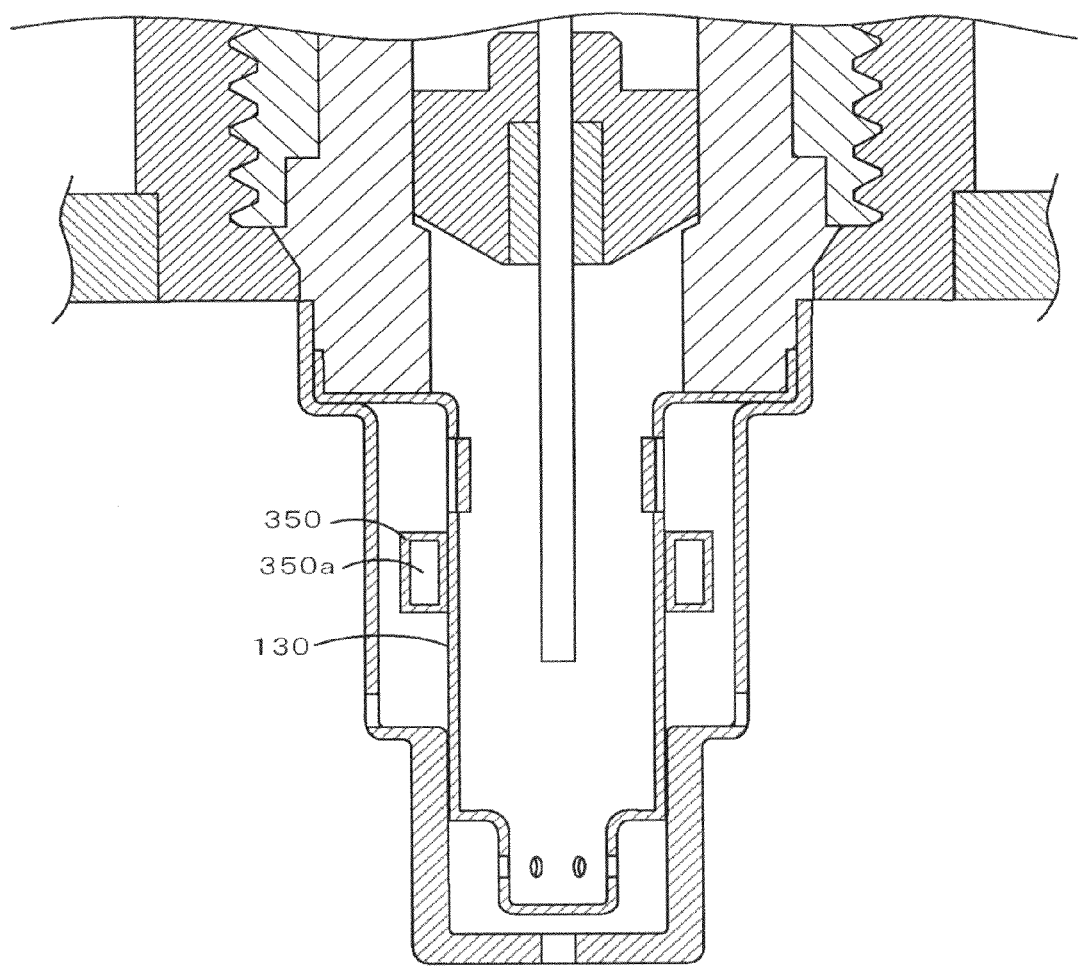
FIG. 5 is a vertical sectional view of an inner wall member 350 in another modified structure.

For example, the inner wall member 150 is formed as the solid member in the above embodiment. In one modified structure shown in FIG. 5, an inner wall member 350 is formed to have an inner enclosed space 350a. In the inner wall member 350 of this structure, a predetermined gas may be enclosed in the inner enclosed space 350a. The inner wall member of such modified structure is also capable of storing the surrounding heat and effectively prevents a temperature decrease of the sensor element 110, compared with a structure without the inner wall member. The predetermined gas enclosed in the enclosed space 350a formed in the inner wall member 350 preferably has a specific heat equivalent to or higher than the specific heat of the inner protection cover 130.

Figure 6:
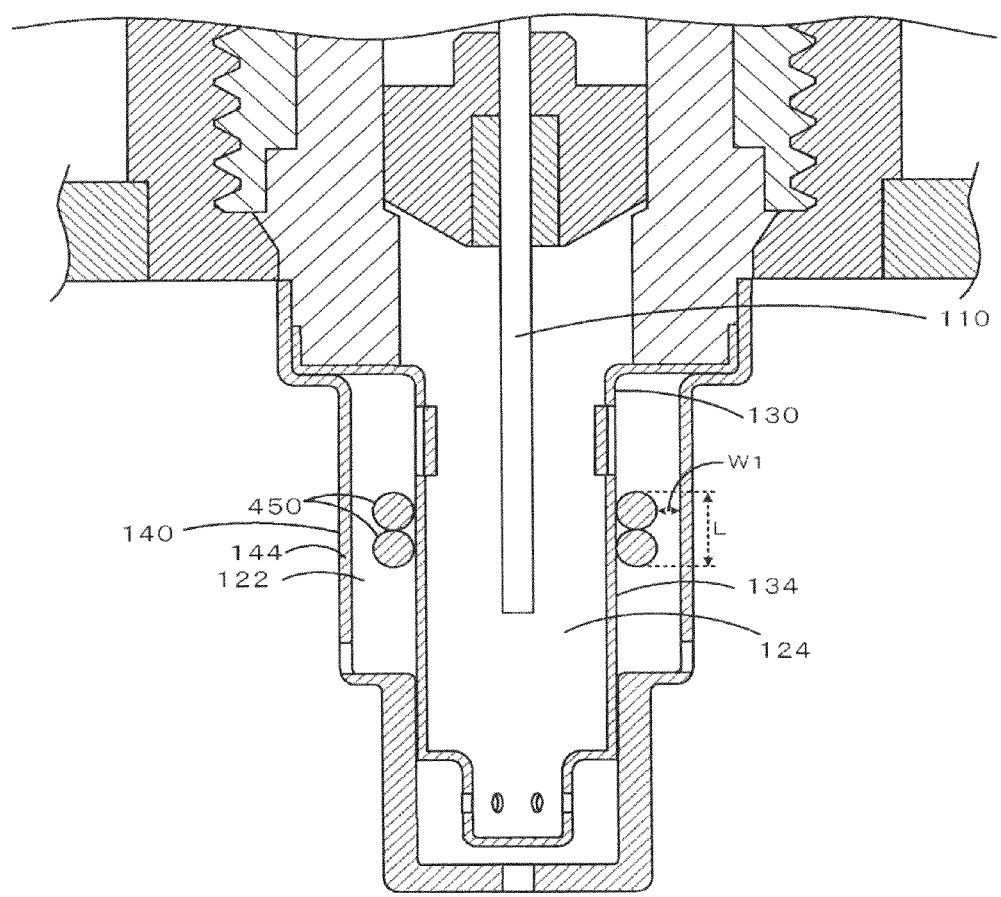
FIG. 6 is a vertical sectional view of an inner wall member 450 in still another modified structure.
Figure 7:
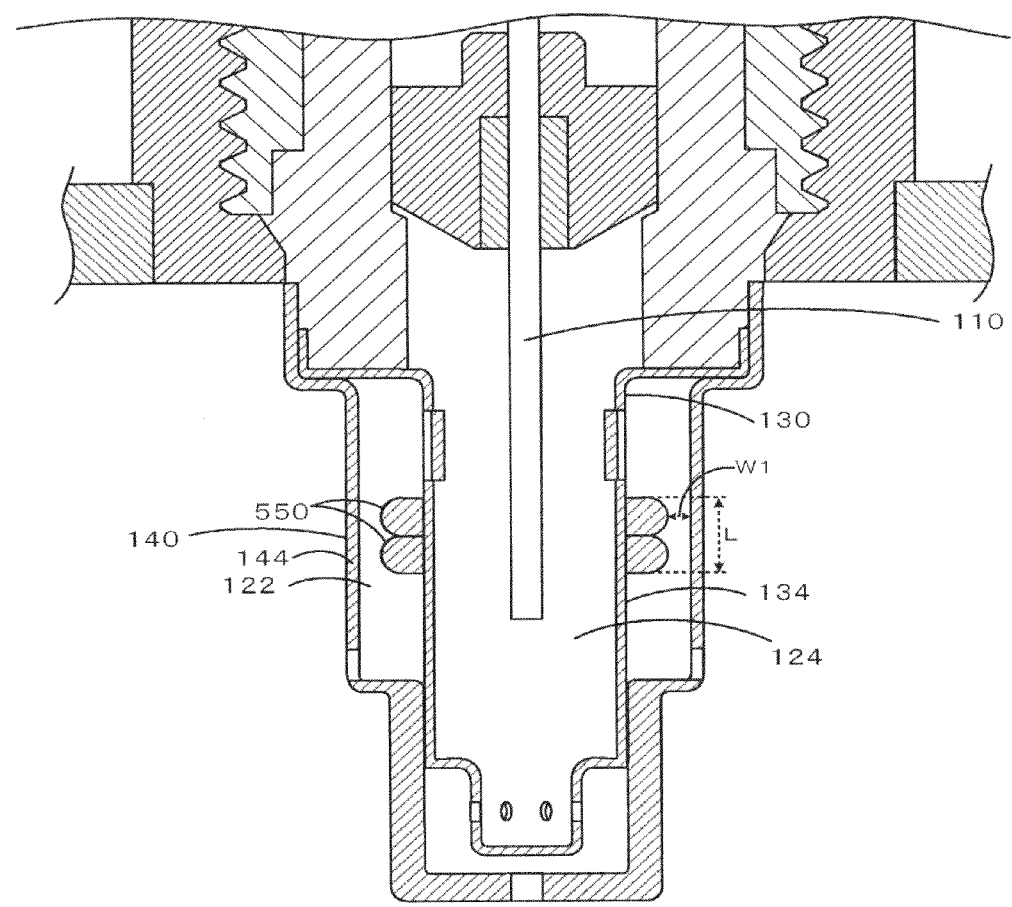
FIG. 7 is a vertical sectional view of an inner wall member 550 in further another modified structure.
Figure 8:
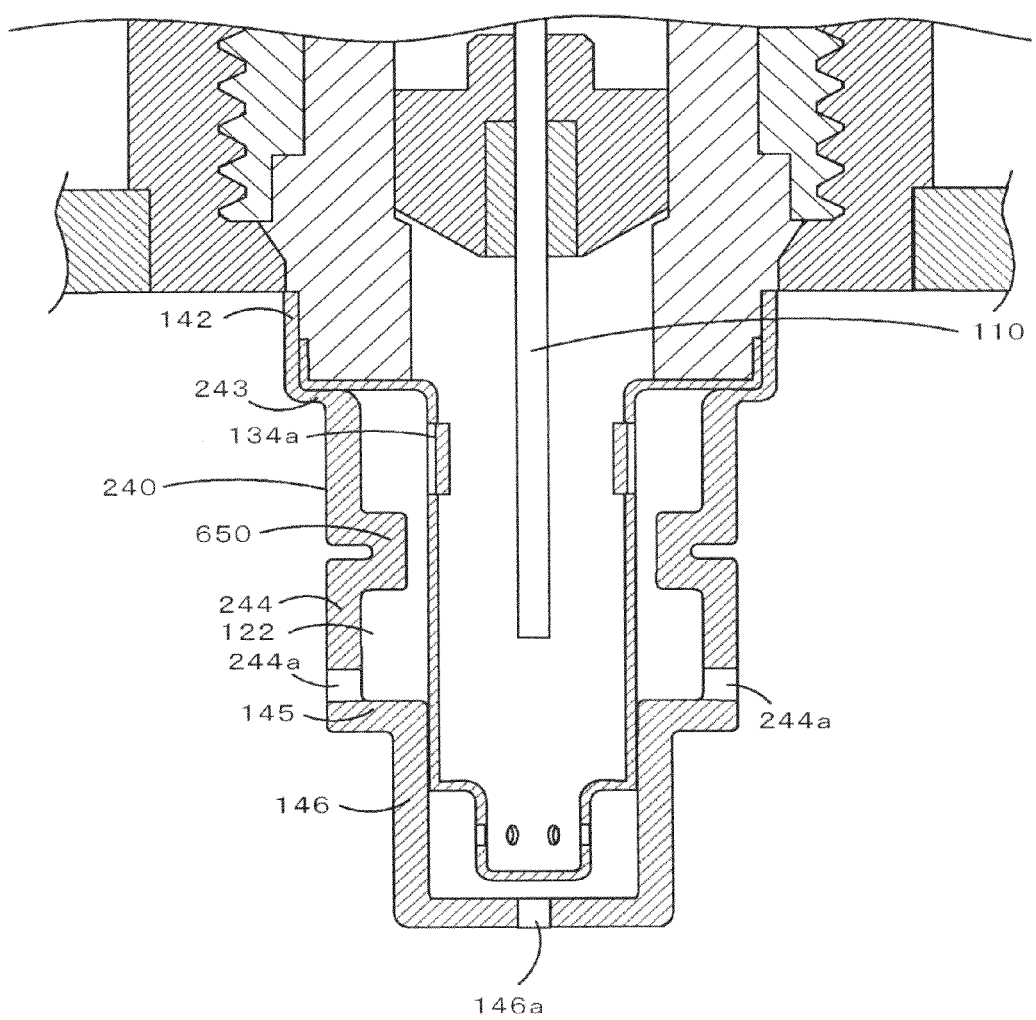
FIG. 8 is a vertical sectional view of an inner wall member 650 and an outer protection cover 240 in still another modified structure.

In the embodiment described above, the inner wall member 150 is attached to the outer circumferential face of the stem section 134 of the inner protection cover 130. This arrangement is, however, not restrictive, but the inner wall member 150 may have any other suitable arrangement to narrow the width of at least part of the gas flow path from the outer gas introduction apertures 144a through the space between the outer protection cover 140 and the inner protection cover 130 to the free end of the sensor element 110. In one modified structure shown in FIG. 6, an inner wall member 450 includes two ring members of a circular vertical section. In another modified structure shown in FIG. 7, an inner wall member 550 includes two ring members of a horseshoe vertical section. In these modified structures, a width W1 of the flow path (corresponding to a difference between the radius of the inner circumferential face of the stem section 144 and a radius of an outer-most circumference of the inner wall member 450 or 550) is less than a difference between a radius of the outer circumferential face of the stem section 134 and the radius of the inner circumferential face of the stem section 144. These structures thus prevent the liquid, such as water, from passing through the gas inflow chamber 122 and reaching the sensor element 110, compared with structures without the inner wall member 450 or 550. The inner wall member may be a non-ring-shaped member. The inner wall member may be attached to the outer protection cover 140. Both the inner protection cover 130 and the outer protection cover 140 may have inner wall members. In the embodiment described above, the inner wall member 150 is formed as a separate member from the inner protection cover 130 and the outer protection cover 140. This separate structure facilitates fabrication of the gas sensor 100, compared with an integrated structure. The inner wall member 150 may, however, be formed from one material to be integral with the inner protection cover 130 or with the outer protection cover 140. In one modified structure shown in FIG.

8, an inner wall member 650 may be integrally formed with an outer protection cover 240 from one identical material. In the outer protection cover 240, part of a stem section 244 is pressed or stamped to form the inner wall member 650. This modified structure also has a narrower-width flow passage formed by the inner wall member 650 in the flow path from outer gas introduction apertures 244a toward the inner gas introduction apertures 134a and prevents the liquid, such as water, from passing through the gas inflow chamber 122 and reaching the sensor element 110, compared with a structure without the inner wall member 650. The stem section 244 and the inner wall member 650 are formed to have the same thickness, which is greater than the thickness of the stem section 144 shown in FIG. 2. This structure facilitates pressing or stamping formation of the inner wall member 650, compared with pressing or stamping part of the stem section 244 to make the inner wall member 650 thicker than the stem section 244. The stem section 244 having the greater thickness than the thickness of the stem section 144 is capable of storing a greater amount of the surrounding heat than the stem section 144, while the inner wall member 650 is capable of storing the surrounding heat, like the inner wall member 150. This structure accordingly has the enhanced effect of preventing a temperature decrease of the sensor element 110.

Figure 9:
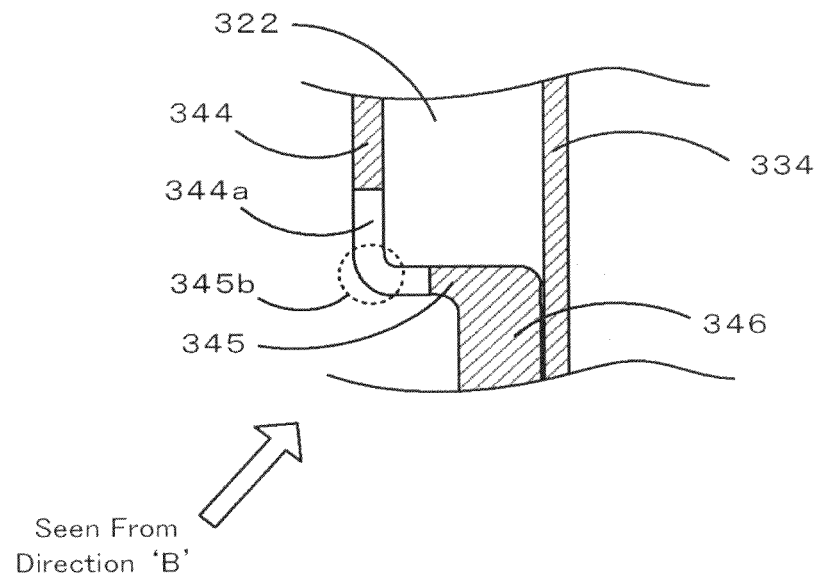
FIG. 9 is a partial sectional view of an outer gas introduction aperture 344a in one modified structure.
Figure 10:
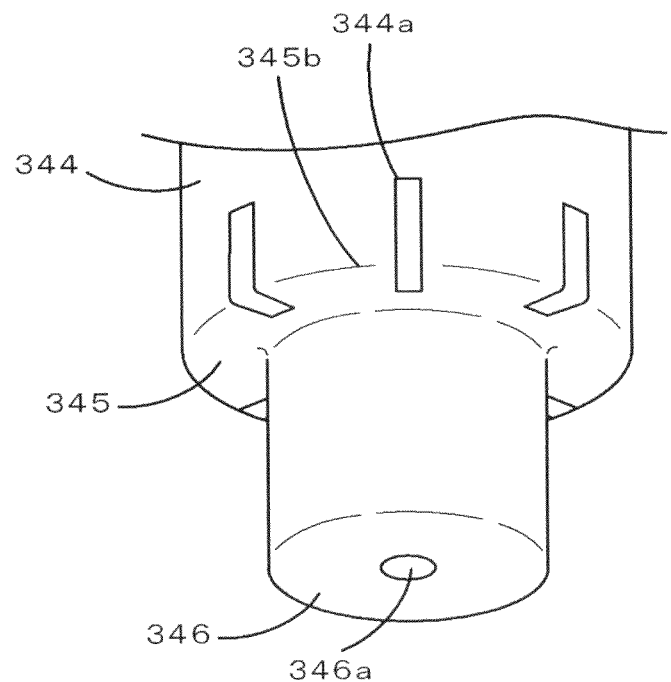
FIG. 10 is a view seen from a direction 'B' of FIG. 9.
Figure 11:
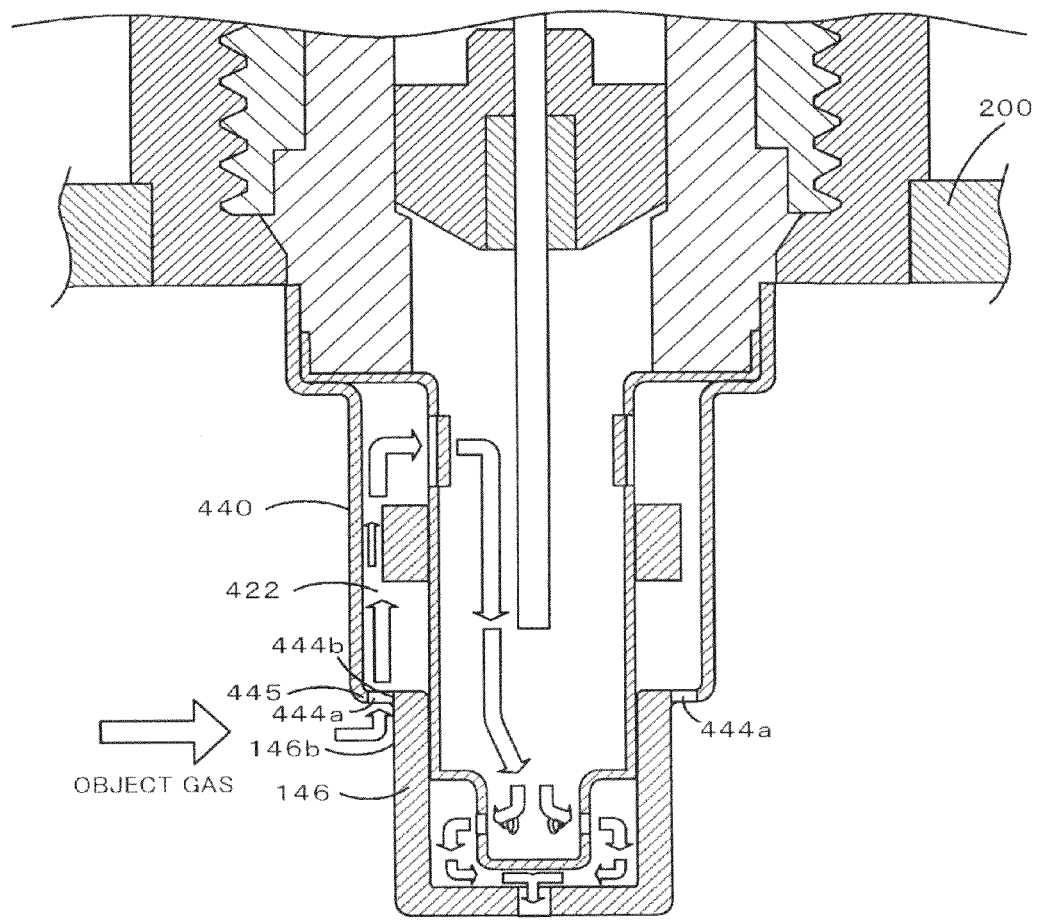
FIG. 11 is a vertical sectional view of outer gas introduction apertures 444a in another modified structure.

In the structure of the embodiment described above, the outer gas introduction apertures 144a are formed in such a manner that the lower-most face 144b of the inner circumferential face of each outer gas introduction aperture 144a is aligned with the upper face 145a of the step element 145. This arrangement is, however, not restrictive, but the outer gas introduction apertures 144a may be formed in any other suitable shape that does not prevent the liquid entering the gas inflow chamber 122 via the outer gas introduction apertures 144a from being discharged from the outer gas introduction apertures 144a. FIG. 9 is a partial sectional view of an outer gas introduction aperture 344a in one modified structure, and FIG. 10 is a view seen from a direction 'B' of FIG. 9. The outer gas introduction aperture 344a is formed to include a rim 345b as a boundary between a step element 345 and a stem section 344. The outer gas introduction aperture 344a of this shape enables the liquid entering a gas inflow chamber 322 to be more readily discharged via the outer gas introduction aperture 344a and lowers a probability that the liquid reaches the sensor element 110, compared with the shape of the outer gas introduction aperture 144a in the embodiment described above. Unlike the outer gas introduction aperture 144a formed as a circular hole, the outer gas introduction aperture 344a is formed as a slit as shown in FIG. 10. The circular aperture and the slit aperture having practically equal areas assure the substantially equivalent inflow easiness of the object gas. The inflow easiness of the liquid, however, changes with a variation in width of the slit, due to the surface tension. The outer gas introduction aperture 344a may thus be formed in a slit having a predetermined width (for example, in a range of 0.1 to 0.5 mm). The slit aperture of this width range interferes with the inflow of only the liquid and more effectively prevents the liquid from entering inside of the outer protection cover, compared with the circular aperture of the same area. FIG. 11 is a vertical sectional view of outer gas introduction apertures 444a in another modified structure. The outer gas introduction apertures 444a are open to pass through a step element 445 in a direction perpendicular to the flow direction of the object gas in the piping 200. An inner circumferential face 444b of each outer gas introduction aperture 444a closest to a central axis of an outer protection cover 440 is arranged to be aligned with part of an outer circumferential face 146b of the edge section 146. This arrangement causes the object gas running in the piping 200 to initially hit against the outer circumferential face 146b and subsequently enter a gas inflow chamber 422 via the outer gas introduction apertures 444a. The liquid, such as water, flowing with the object gas in the piping 200 accordingly adheres to the outer circumferential face 146b. Compared with the arrangement of the outer gas introduction apertures 144a in the embodiment shown in FIG. 2, the arrangement of the outer gas introduction apertures 444a more effectively prevents the invasion of the liquid into the outer protection cover 440 via the outer gas introduction apertures 444a. Alternatively the inner circumferential face 444b may not be aligned with the outer circumferential face 146b.

Figure 12:
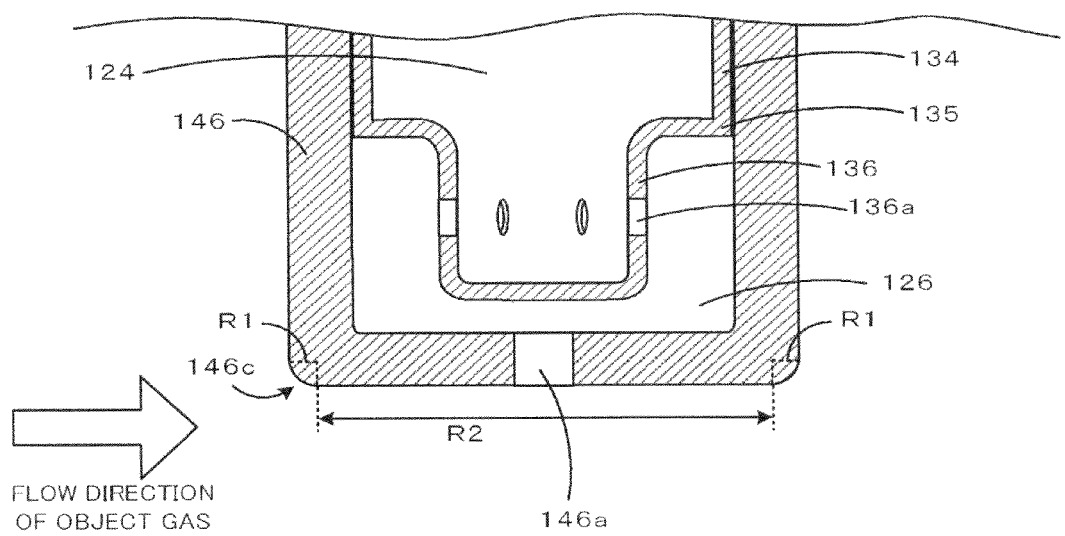
FIG. 12 is an enlarged partial sectional view of an edge section 146 of FIG. 2.

In the embodiment described above, the desired shape of the edge section 146 makes the laminar flow of the object gas in the outer periphery of the outer gas discharge aperture 146a. FIG. 12 is an enlarged partial sectional view of the edge section 146 of FIG. 2. Adequate values are set to a radius R1 of a curved surface of a rim 146c of the edge section 146 and a diameter R2 of a bottom face of the edge section 146 other than the rim 146c shown in FIG. 12. Such setting makes the laminar flow of the object gas in the outer periphery of the outer gas discharge aperture 146a. Even when there is a liquid on the flow of the object gas, formation of the laminar flow effectively interferes with invasion of the liquid into the outer protection cover 140 via the outer gas discharge aperture 146a. This arrangement lowers the pressure in the outer periphery of the outer gas discharge aperture 146a than the internal pressure of the gas outflow chamber 126, so that the object gas in the gas outflow chamber 126 is immediately discharged from the outer gas discharge aperture 146a. Namely this arrangement enables the object gas inside the protective cover 120 to be replaced within a shorter time period, thus enhancing the response of the sensor element 110.

In the embodiment described above, the protective cover 120 desirably has the smaller volume. The smaller volume enables the object gas inside the protective cover 120 to be replaced within a shorter time period, thus enhancing the response of the sensor element 110.

In the structure of the embodiment described above, there are six inner gas introduction apertures 134a arranged at equal intervals around the stem section 134. The number of the inner gas introduction apertures 134a is, however, not limited to six, and the interval of the inner gas introduction apertures 134a may not be the equal interval.

EXAMPLES

Example 1

Comparative Example 1

A gas sensor 100 having the structure of the embodiment described above was fabricated as Example 1, where the width W was 0.7 mm, the length L was 1.8 mm, the inner diameter of the inner wall member 150 was 6.4 mm, and SUS310 was used as the material of the inner protection cover 130, the outer protection cover 140, and the inner wall member 150. Six outer gas introduction apertures 144a were formed at equal intervals around the stem section 144. The inner gas discharge apertures 136a were not formed in the edge section 136 of the inner protection cover 130, because of the reason discussed later. The heating value of the built-in heater included in the sensor element 110 was feedback controlled to keep the sensor element 110 at a constant temperature of 850° C. A gas sensor 100 having the same structure as Example 1 except omission of the inner wall member 150 was fabricated as Comparative Example 1.

Evaluation Test 1

Figure 13:
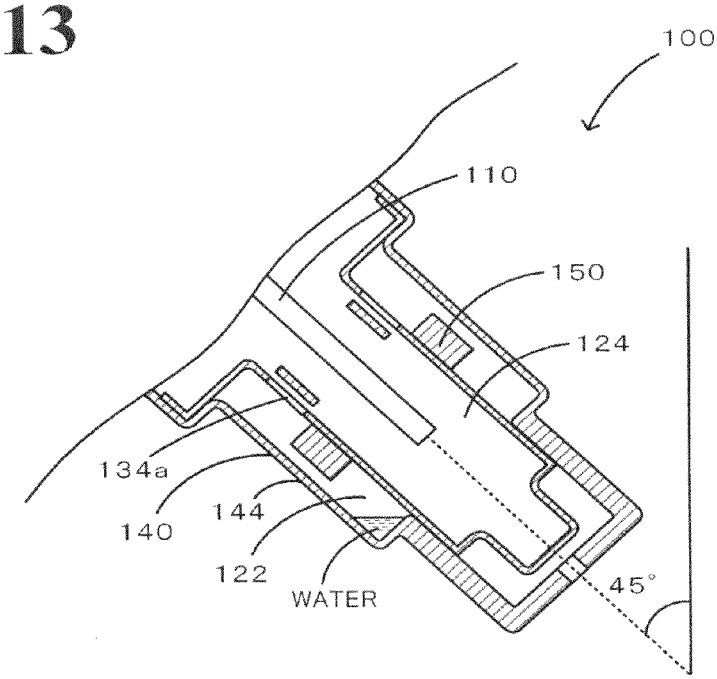
FIG. 13 is an explanatory view of Evaluation Test 1.
Figure 14:
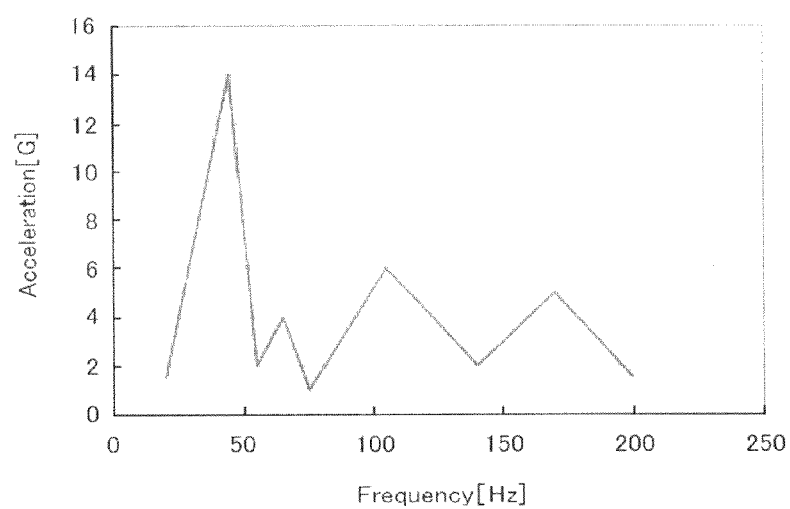
FIG. 14 is a graph showing a vibration condition in Evaluation Test 1.

The fabricated gas sensors 100 of Example 1 and Comparative Example 1 were evaluated. The sensor element 110 was inclined at 45 degrees relative to a vertical direction, while 100 μl of water was held in a space closer to the outer gas introduction apertures 144a across the inner wall member 150 in the gas inflow chamber 122 (a corresponding space in Comparative Example 1). The gas sensor 100 of Example 1 in this state is shown in FIG. 13. The gas sensor 100 was inclined, such that the water held in the gas inflow chamber 122 was not spilled via the outer gas introduction apertures 144a out of the outer protection cover 140. Vibration shown in FIG. 14 was applied in the vertical direction for 30 minutes to the gas sensor 100 of Example 1 and to the gas sensor 100 of Comparative Example 1 each inclined at 45 degrees. The behavior of the water in the gas inflow chamber 122 was observed, and the amount of water accumulated in the sensor element chamber 124 after the application of the vibration was measured. In the gas sensor 100 of Example 1, there was no invasion of water into the space closer to the inner gas introduction apertures 134a across the inner wall member 150 in the gas inflow chamber 122. Namely the sensor element chamber 124 had no water. In the gas sensor 100 of Comparative Example 1, on the other hand, the total amount 100 μl of water invaded into the corresponding space to the space closer to the inner gas introduction apertures 134a across the inner wall member 150 in the gas inflow chamber 122 of Example 1. The sensor element chamber 124 had 20 of water. In the structure of Example 1, the inner wall member 150 partially narrowed the width of the gas flow path in the gas inflow chamber 122. This arrangement lowers the probability that water enters the space closer to the inner gas introduction apertures 134a across the inner wall member 150 in the gas inflow chamber 122. No invasion of water in Example 1 may be ascribed to this arrangement. Both the gas sensors 100 of Example 1 and Comparative Example 1 were fabricated without the inner gas discharge apertures 136a, in order to prevent the water moving from the gas inflow chamber 122 into the sensor element chamber 124 from being discharged via the inner gas discharge apertures 136 and allow for accurate measurement of the water present in the sensor element chamber 124 after the application of the vibration.

Example 2

Comparative Example 2

A gas sensor 100 having the same structure as Example 1 except formation of six inner gas discharge apertures 136a arranged at equal intervals around the edge section 136 of the inner protection cover 130 was fabricated as Example 2. A gas sensor 100 having the same structure as Example 2 except omission of the inner wall member 150 was fabricated as Comparative Example 2.

Evaluation Test 2

Figure 15:
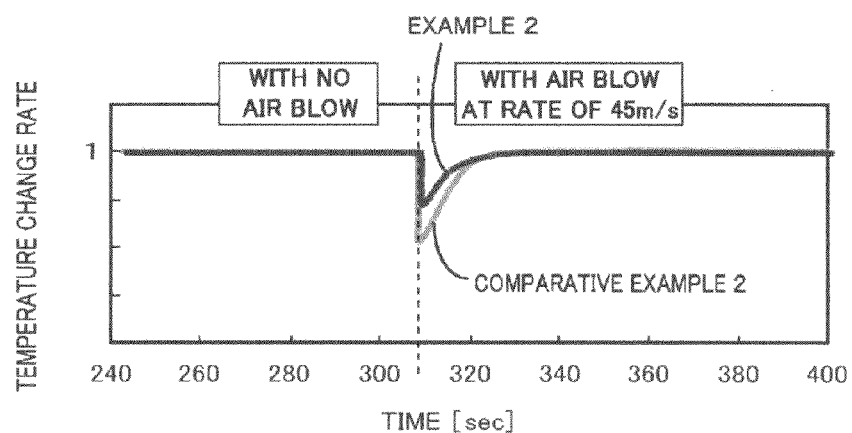
FIG. 15 is a graph showing temperature changes of sensor elements 110 in Evaluation Test 2.
Figure 16:
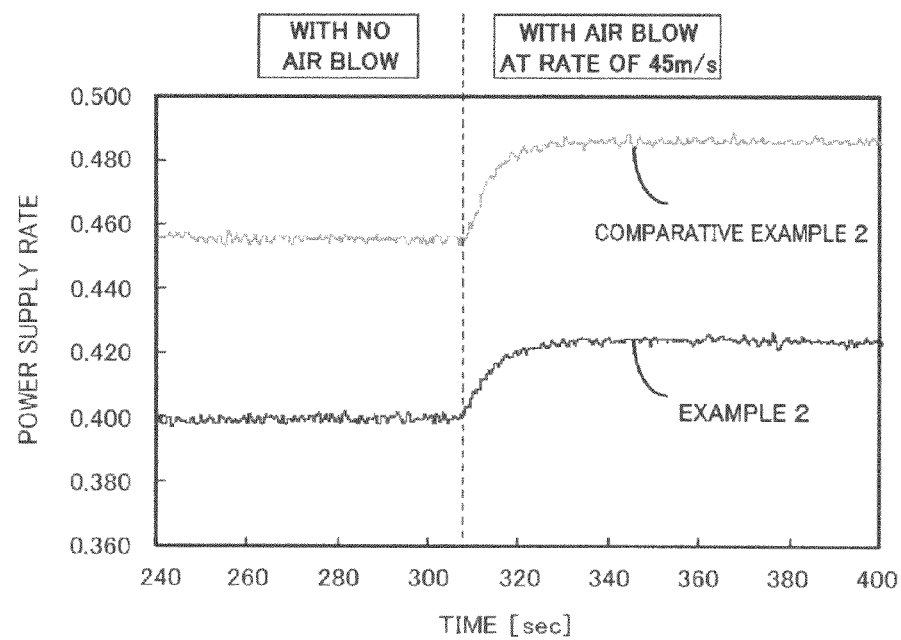
FIG. 16 is a graph showing changes in heater power supply rate in Evaluation Test 2.

The gas sensors of Example 2 and Comparative Example 2 were respectively attached to the piping as shown in FIG. 1. The piping was filled with the air. After the piping was stood still with no air blow for 310 seconds, the air was blown in the piping at a flow rate of 45 m/s. Temperature variations of sensor elements 110 in Example 2 and in Comparative Example 2 are shown in FIG. 15. Variations in heater power supply rate (rate of a power output to a maximum power output of 15 W of the heater) of the sensor element 110 in Example 2 and in Comparative Example 2 are shown in FIG. 16. As shown in FIG. 15, the sensor element 110 of Example 2 had a smaller temperature change even in the event of an abrupt variation of the air flow rate. This may be ascribed to the function of the inner wall member 150 that stores the surrounding heat and thereby prevents an abrupt temperature change of the sensor element 110. As shown in FIG. 16, the heater power output of the sensor element 110 in Example 2 is smaller than that in Comparative Example 2, irrespective of the presence or the absence of the air blow. This may be ascribed to the function of the inner wall member 150 that stores the surrounding heat and thereby enhances the heat retention effect of the sensor element 110. Compared with the structure without the inner wall member 150, the structure with the inner wall member 150 reduces the heater power output required to keep the sensor element 110 at a constant temperature.

The structure of the invention including a protective cover with an inner wall member is not restrictively applied to a gas concentration detection sensor of detecting the concentration of a selected gas included in an object gas, such as the gas sensor 100 described above, but is applicable to any sensor with a sensor element having the potential of liquid-inducing trouble, for example, cracking caused by the liquid, such as water, adhering to the sensor element.

The present application claims priority from the Japanese Patent Application No. 2009-270400 filed on Nov. 27, 2009, the entire contents of which are by reference incorporated herein.

What is claimed is:

1. A gas concentration detection sensor, comprising:
a sensor element that detects concentration of a selected gas included in an object gas;
a first protection cover that covers over the sensor element and has a first gas introduction aperture allowing for a flow of the object gas from outside to inside of the first protection cover;
a second protection cover that covers over the first protection cover and has a second gas introduction aperture allowing for a flow of the object gas from outside to inside of the second protection cover;
a gas flow path that runs from the second gas introduction aperture through a space between the first protection cover and the second protection cover to the first gas introduction aperture, enters inside of the first protection cover via the first gas introduction aperture, and reaches an edge of the sensor element,
wherein at least one of the first protection cover and the second protection cover is provided with an inner wall member of a solid form or a hollow form that creates an internal enclosed space arranged to at least partially narrow a width of a flow path from the second gas introduction aperture to the first gas introduction aperture
wherein the first protection cover has a first gas discharge aperture that is formed in a circumferential wall of the first protection cover at a lower position than the edge of the sensor element, the second protection cover has a second gas discharge aperture formed in a bottom face of the second protection cover, and
the object gas reaching the sensor element passes through the first gas discharge aperture by a radially outward flow in a direction from a center to an outer circumference of the first protection cover and is discharged out via the second gas discharge aperture.

2. The gas concentration detection sensor according to claim 1, wherein the first protection cover is provided with the inner wall member.

3. The gas concentration detection sensor according to claim 1, wherein the inner wall member has a specific heat equivalent to or higher than a specific heat of the first protection cover.

4. The gas concentration detection sensor according to claim 1, wherein the gas flow path causes the object gas to flow in from the second gas introduction aperture, pass through the space between the first protection cover and the second protection cover to the first gas introduction aperture by flowing in a direction from a free end to a base end of the sensor element, enter inside of the first protection cover via the first gas introduction aperture, flow in a direction from the base end to the free end of the sensor element, and reach the edge of the sensor element.

5. The gas concentration detection sensor according to claim 1, wherein the inner wall member is formed separately from the first protection cover and the second protection cover.

6. The gas concentration detection sensor according to claim 1, wherein the first protection cover has a guide element that controls a flow of the object gas flowing into the first protection cover via the first gas introduction aperture to interfere with a direct flow of the object gas toward the sensor element.

7. The gas concentration detection sensor according to claim 1, wherein the bottom face of the second protection cover with the second gas discharge aperture formed therein is made thicker than a portion of the second protection cover with the second gas introduction aperture formed therein.

8. The gas concentration detection sensor according to claim 1, wherein the first protection cover has a first stem section with the first gas introduction aperture formed therein, a bottomed cylindrical first edge section having a smaller diameter than a diameter of the first stem section, and a first step element connecting the first stem section with the first edge section, the second protection cover has a second stem section with the second gas introduction aperture formed therein, a bottomed cylindrical second edge section having a smaller diameter than a diameter of the second stem section, and a second step element connecting the second stem section with the second edge section, a lower portion of an outer circumferential face of the first stein section is in contact with an upper portion of an inner circumferential face of the second edge section, a gas inflow chamber is defined by the first stem section, the second stem section, and the second step element, and the object gas in the gas flow path enters the gas inflow chamber via the second gas introduction aperture and reaches the first gas introduction aperture.

9. The gas concentration detection sensor according to claim 8, wherein the second gas introduction aperture is formed such that a lower-most face of an inner circumferential face of the second gas introduction aperture is aligned with an upper face of the second step element.

* * * * *